United States Patent [19]

Nambu et al.

[11] Patent Number: 4,958,626

[45] Date of Patent: Sep. 25, 1990

[54] METHOD FOR APPLYING ELECTROMAGNETIC WAVE AND ULTRASONIC WAVE THERAPIES

[75] Inventors: Masao Nambu, Yokohama; Tsutomu Watari, Tokyo; Tomoyuki Sakamoto, Kokubunjimachi; Kazuo Akojima, Yachiyo, all of Japan

[73] Assignee: Nippon Oil Co., Ltd., Tokyo, Japan

[21] Appl. No.: 165,417

[22] Filed: Feb. 29, 1988

Related U.S. Application Data

[63] Continuation-in-part of Ser. No. 39,504, Apr. 17, 1987, abandoned.

[30] Foreign Application Priority Data

Apr. 22, 1986 [JP] Japan .................................. 61-91228

[51] Int. Cl.$^5$ ........................ A61B 17/00; A61N 5/00
[52] U.S. Cl. .................................... 128/24 A; 128/804
[58] Field of Search ................. 128/660.01, 663.01, 128/804, 653

[56] References Cited

U.S. PATENT DOCUMENTS

| | | | |
|---|---|---|---|
| 2,242,886 | 5/1941 | Hirschland et al. | 128/804 |
| 2,789,557 | 4/1957 | Davis, Jr. | 128/24 A |
| 2,814,298 | 11/1975 | Argento | 128/804 |
| 4,717,378 | 1/1988 | Perrault et al. | 128/660.01 |

FOREIGN PATENT DOCUMENTS 0215701 11/1984 Fed. Rep. of Germany ... 128/24 A

*Primary Examiner*—Francis Jaworski
*Attorney, Agent, or Firm*—Jordan and Hamburg

[57] ABSTRACT

A method for applying electromagnetic wave and ultrasonic wave therapies is provided. According to the method, a material simulating a living tissue is applied and pressed onto a surface of a human body so that the material is intimately contacted with the body surface with substantially no spaces present therebetween. Electromagnetic or ultrasonic wave is generated and irradiated to the body through the material. The material comprises a hydrogel having a high water content. The hydrogel is prepared by the steps of casting an aqueous polyvinyl alcohol solution into a mold, cooling the cast aqueous solution to obtain a cooled frozen mass and thawing the cooled frozen mass. The cooling and thawing steps may be repeated up to eight cycles. The hydrogel is also prepared by subjecting the cooled frozen mass to a partial dehydration step in vacuum.

12 Claims, 1 Drawing Sheet

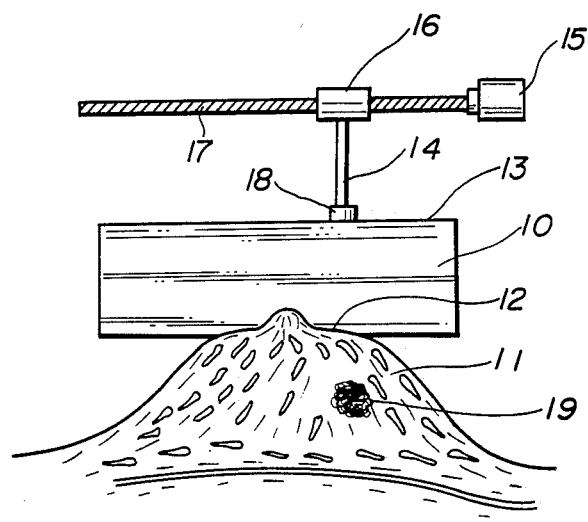

METHOD FOR APPLYING ELECTROMAGNETIC WAVE AND ULTRASONIC WAVE THERAPIES

CROSS-REFERENCE TO RELATED APPLICATION

This application is a continuation-in-part application of U.S. Ser. No. 39,504 filed Apr. 17, 1987, now abandoned.

BACKGROUND OF THE INVENTION

1. Field of the Invention

The present invention relates to a method for applying electromagnetic wave and ultrasonic wave therapies.

2. Related Art Statement

A fresh cut piece of an animal tissue or a material for simulating a living tissue made of, for example, KONNYAKU (devil's tongue), gelatin (jelly), agar, rubber or starch paste, has been proposed to prepare a phantom (a model for stimulating a living tissue) used in the practice of electromagnetic wave therapy (thermal therapy), radiotherapy or ultrasonic wave therapy. Although some of these known materials have been used practically, they have many problems.

A phantom simulating a living tissue is required for the therapy, in which electromagnetic waves or ultrasonic waves are used, for the following reasons.

When a lesion site is irradiated with a radioactive ray, the normal or healthy tissue present between the source of radioactive ray and the lesion site cannot be neglected. If the living tissue interposed between the source of radioactive ray and the lesion site is flat and has an uniform thickness, the attenuation of the radioactive ray by the interposed tissue can be estimated to control the radioactive ray so that the lesion site is irradiated with a desired dosage of radioactive ray. However, since the surface of the patient body is generally not flat and even, the interposed tissue cannot be closely estimated as an equivalent attenuating region (a flat plate-like region having a uniform thickness) to pose a problem for execution of radiotherapy. In order to overcome the problem, it has been tried to flatten the body surface or the surface of the interposed tissue. Although a method of compressing the body surface to deform the vicinity of the body surface has been adopted as a tentative measure, the deformation of the body surface tissue (flattening of the body without invading the tissue) is limited and only a limited effect is obtained by such a measure. Accordingly, it is a common practice to apply a material for simulating the living tissue on the surface of the body or skin, followed by molding the living tissue simulating material to have desired shape and dimensions to provide a flat surface which is normal to the direction from the lesion site to the source of the ray. Thus, there is a demand for a material which can simulate a living tissue and moldable to have a desired shape to be closely fitted on the surface of the patient's body and which exhibits a radioactive ray attenuation equivalent to that of the living tissue.

It is also desired that the material has characteristics under the irradiation of a radioactive ray similar to those of the living tissue in order that a model for examining the details of the attenuation of the radioactive ray in the living body. In the ultrasonic wave therapy (thermal therapy), a major portion of the ultrasonic waves is reflected by a small amount of air bubbles present between the surface of the skin and a probe or terminal for discharging ultrasonic waves when the probe or terminal contacts the surface of the patient's body. In order to eliminate such a disadvantageous effect, a material for removing air is interposed between the probe and the surface of the skin. Therefore, there is a demand for a material which can be applied closely to both of the probe and the surface of the skin and has ultrasonic properties (impedance) equivalent to that of the living tissue.

The temperature of the lesion site internally of the patient's body irradiated with an ultrasonic wave, radio wave or microwave must be maintained at a temperature of from 41.5° C. to 43° C. for a predetermined time when thermal therapy is applied for the medical treatment of cancer. Prior to the practical medical treatment, it is essential to learn the temperature rise in the internal sites in the patient's body under varying irradiation conditions (frequency, duration of irradiation, etc.). For such purpose, a material having thermal characteristics equivalent to those of the living tissues is demanded to prepare a model for simulating the living body.

It will be seen from the foregoing that there has been a demand for a material for simulating a living tissue to be used in medical treatment in which an ultrasonic wave or an electromagnetic wave is used. One example of the materials for simulating a living tissue is a fresh tissue of a killed animal extracted immediately after killing. However, it is difficult to have such a fresh animal tissue at every moment when it is demanded, and the electromagnetic and ultrasonic properties of the fresh animal tissue are abruptly changed even if such an animal tissue is stored in a cold place (H. F. Bowman, "Ann. Rev. Biophys. Bioeng.", 4, 43 (1975); F. K. Storm et al, "Int. J. Radiation Oncology Biol. Phys.", 8, 865 (1982); and R. V. Damadian, U.S. Pat. No. 3,789,832 (1974)). Accordingly, searching works for natural or artificial materials for simulating living tissues have been continued.

Since the living tissues generally have the electromagnetic and ultrasonic properties resembling those of water, it has been proposed to use water or a hydrogel having a high water content is used as a material for simulating a living tissue. For instance, a water bag (a pouch containing water) is placed on the surface of the skin for flattening the irradiated surface in the radiotherapy and a water bag is also placed on the surface of the skin for excluding the disturbance by air (for preventing reflection or diffusion and for matching the impedances) in the thermal therapy in which an electromagnetic wave or an ultrasonic wave is used (U.S. Pat. No. 2,789,557). However, it is difficult to achieve stable operation by the use of a water bag due to deformation and dislocation of the bag. In order to avoid such disadvantages, the use of a high water content hydrogel, such as jelly, KONNYAKU or agar, has been proposed. Since they contain 96 to 98% of water, they have the properties resembling those of the living tissues, and yet they have tentative shape-retaining properties. However, jelly (gelatine) is so soft and easily deformed. Agar is fragile and easily broken, and KONNYAKU is greatly deformed or shrunked due to syneresis after it is molded. In addition, these known hydrogels are too high in water content as compared with those of the living tissues (the water content of soft living tissues ranges from 70 wt% to 80 wt%), and thus they are unsatisfactory in this respect. In order to prepare a material having properties closer to those of the living tissues, it has been proposed to replace a portion of water contained in the known hydrogel by n-propyl alcohol, glycerine, polyethylene glycol, sodium carbonate or graphite powders. However, the qualities of the materials from natural resources, such as agar and KONNYAKU, are unstable so that it is difficult to supply stable standardized products.

With the aim of preventing deformation of the aforementioned gelatine product, it has been tried to cross-link gelatin by formalin or glutaraldehyde. (E. L. Madsen et al, "Ultrasound in Med. Biol.", 8, (4) 381 (1982); E. L. Madsen et al, "Mag. Res. Imag." 1, 135 (1982); and E. L. Madsen et al, "Am. Assoc. Phys. Med.", 5, 391 (1978)). However, it was difficult to prepare a molded product of standardized quality due to uneven gelation or uneven cross-linking. High water content hydrogels prepared from polysaccharides, such as carrageenan or alginic acid, are inferior in mechanical strength similarly to agar.

Although polyacrylamide, one of the well known synthetic materials from which a high water content hydrogel may be prepared, has an advantage that a hydrogel having a controlled water content equivalent to those of the living tissues (70 to 85%) can be prepared therefrom, it is difficult to prepare a molded product of uniform quality therefrom due to difficulty in uniform gelation. The polyacrylamide gel has a further disadvantage that it is fragile and apt to be broken during the handling by pincettes. U.S. Pat. No. 2,814,298 discloses a pad made of butyl rubber loaded with titanium dioxide which is interposed between a vibrator and a surface of a human body when applying ultrasonic wave, to thereby reduce energy loss due to reflection from the surface of the body. By the use of the pad, reflection loss is somehow improved. However, energy is greatly lost when passing through the pad is that such a pad is not preferred.

U.S. Pat. No. 2,242,886 discloses a condenser electrode for use in short-wave and ultra-short wave therapy comprising an electrode plate and a paraffin block attached thereto. However, paraffin has small specific gravity and excessively low acoustic impedance, thereby causing reflection loss at the interface.

Since it is difficult to prepare a material for simulating the living tissues by the use of a water bag or a natural or synthetic gel, it is a common practice to dip the diseased site in water. For example, when mammary cancer is irradiated with an ultrasonic wave, the patient is laid in the prone posture and the downwardly extending mamma is dipped in a water reservoir to ensure removal of air bubbles from the vicinity of the surface of mamma prior to exposure to the ultrasonic wave. Although it is possible to dip mamma, the limbs, the abdominal region, the chest and the neck, a large water reservoir is required to pose inconvenience in practical operation. The face, head, eye and other internal organs cannot be treated in such condition that they are dipped in water.

OBJECTS AND SUMMARY OF THE INVENTION

Accordingly, a primary object of this invention is to provide a method for applying electromagnetic wave and ultrasonic wave therapies, using a material for simulating a living tissue to be used in the physical treatments (therapies in which an electromagnetic wave or an ultrasonic wave is used), the material being made of a high water content hydrogel which has ultrasonic and electromagnetic properties equivalent to those of living tissues and being soft and hardly fluidized and resistant to breakdown.

A further object of this invention is to provide a method for applying electromagnetic wave and ultrasonic wave therapies, using a material made of a high water content hydrogel and having a shape retaining property at 37° C. and being moldable to have a desired shape and to be used for a long time while retaining the molded shape.

A further object of this invention is to provide a method for applying electromagnetic wave and ultrasonic wave therapies, using a material for simulating a living tissue which is excellent in softness and rubber-like elasticity and can be closely fitted on the surface of the skin to be treated as far as it is molded to have a contour to profile the operated site, and which has a sufficient mechanical strength to be applied to the desired site repeatedly.

A further object of this invention is to provide a material for simulating may a living tissue which may be sterilized by a sterilizing solution or irradiation with gamma-ray without being broken or deteriorated to be ready for application on the surface of the skin applied to a surface of the human body.

A further object of this invention is to provide a method for applying electromagnetic wave and ultrasonic wave therapies, using a material for simulating a living tissue which is prepared from an aqueous solution of a polyvinyl alcohol only by thermal hysteresis at low temperature or through repeated freezing-thawing steps or processing under a reduced pressure without the use of any acids, alkali, chemical reagents or cross-linking agents harmful to the living tissue.

A further object of this invention is to provide a method for applying electromagnetic wave and ultrasonic wave therapies, using a material for simulating a living tissue which does not contain any harmful material and which is inactive to the living tissue so as to be applied repeatedly on the surface of the skin without causing inflammation.

With the aforementioned objects in view, the present invention provides a method for applying electromagnetic wave and ultrasonic wave therapies comprising applying a material simulating a living tissue to a surface of a human body, pressing the material onto the surface of the human body so that the material is intimately contacted with the surface of the human body with substantially no spaces present therebetween, generating a wave selected from the group consisting of electromagnetic wave and ultrasonic wave and irradiating the wave to the human body through the material, the material simulating the living tissue comprising hydrogel having a high water content and being prepared by a process comprising a casting step of casting an aqueous solution containing more than 8 wt% and not more than 50 wt% of a polyvinyl alcohol having a degree of hydrolysis of not less than 95 mol % and an average polymerization degree of not less than 1000 into a mold having desired shape and dimensions, a freezing step of cooling the cast aqueous solution to a temperature of not higher than −(minus) 10° C. to obtain a cooled frozen mass, and a thawing step of thawing the cooled frozen mass.

In the aforementioned method, instead of the above hydrogel there may be used a hydrogel having a high water content and being prepared by a process comprising a casting step of casting an aqueous solution containing more than 8 wt% and not more than 50 wt% of a polyvinyl alcohol having a degree of hydrolysis of not less than 95 mol % and an average polymerization degree of not less than 1000 into a mold having desired shape and dimensions, a freezing step of cooling the cast aqueous solution to a temperature of not higher than —(minus) 10° C. to obtain a cooled frozen mass, and a partial dehydration step of dehydrating the frozen mass in vacuum until the percentage dehydration rate reaches not less than 3 wt%.

BRIEF DESCRIPTION OF THE DRAWINGS

A single figure is a diagammatical partial cross-sectional view showing application of ultrasonic wave to a lesion site of mamma.

DESCRIPTION OF THE INVENTION

The present invention will now be described in detail.

According to the present invention, a material for simulating a living tissue and adapted for use in a physical therapy for treating a lesion site is prepared by a hydrogel having a specific formulation and a high water content.

The polyvinyl alcohol used in the invention should have a degree of hydrolysis of not less than 95 mol %, preferably not less than 98 mol %, and an average polymerization degree of not less than 1000.

In the present invention, an aqueous solution containing the aforementioned polyvinyl alcohol is prepared at the first step. The content of the polyvinyl alcohol in the solution should be in the range of more than 8 wt% and not more than 50 wt%.

In the next step of the process for preparing the hydrogel of the invention, the aqueous solution of the polyvinyl alcohol, as described above and defined in the appended claims, is cast into a mold suited for molding a desired shape for profiling a surface of a local site of human body. Then, the molded mass is cooled to be frozen, and the frozen mass is thawed to prepare a hydrogel having high water content to be offered to the aimed use. The hydrogel having a high water content, provided by the invention, may be subjected to repeated freezing and thawing cycles of up to 8 times or cycles, when it is desired to prepare a material having a high mechanical strength. It is recommended that the freezing and thawing cycles are repeated from 2 to 8 times in consideration of the fact that the advantageous increase in hardness of the hydrogel with the increase in repeated cyclic treatments is saturated substantially by the 8 time repeated cycles and the increase of hardness or strength of the hydrogel is not so high after ninth cycle. (In this connection, reference should be made to Masao Nambu, "Polymer Application", 32, 523 (1983).)

According to another aspect of the invention, the frozen mass may be partially dehydrated in vacuum after it is cooled to be frozen, in lieu of subjecting the same to the freezing and thawing steps. When a partial dehydration step effected in vacuum is adopted, the mechanical strength of the hydrogel is improved as the percentage dehydration rate is increased. It should be noted here that the wording "percentage dehydration rate" as used in this specification and claims is expressed by the percentage reduction of the weight of the cooled and solidified gel. However, it is not necessary to increase the percentage dehydration rate to an extremely high level to form a strong gel, and the percentage dehydration rate should be not less than 3 wt%, preferably in the range of not less than 3 wt% and not more than 35 wt%, to improve the shape-retaining property and machinability of the resultant hydrogel.

The partial dehydration in vacuum means that the hydrogel is dehydrated at some extent under a reduced pressure, and the level of reduced pressure is not particularly limited and ranges, for instance, not higher than 1 mmHg, preferably not higher than 0.1 mmHg and more preferably not higher than 0.08 mmHg. The mold is not particularly restricted as far as a molded product having a desired shape to profile a surface of a local site of a living body is prepared. The thickness (uniformity in thickness or thickness distribution) and the shape and dimensions of the molded product may be properly selected in compliance with the practical circumstances in the applied therapy in which a macrowave, radio wave, gamma-ray, X-ray, neutron, laser beam or ultrasonic wave is used.

According to this invention, the water content of the hydrogel may be varied in consideration of the specific living tissue which is simulated by the hydrogel of the invention. The water content of the hydrogel is determined by the composition of the aqueous solution (or suspension) of polyvinyl alcohol used in the initial step. When the aqueous solution or suspension of polyvinyl alcohol is subjected to partial dehydration step after it has been frozen, the water content of the resultant hydrogel may be determined by calculating the amount of removed water derived at the partial dehydration step. The water content of a hydrogel which is prepared, without being subjected to partial dehydration, only by the freezing and thawing processings (or subjecting to repeated freezing and thawing cycles) may be easily calculated since the aqueous solution of polyvinyl alcohol used at the initial step has been gelled without removal of water therefrom.

A material prepared by the present invention may have a predetermined water content ranging preferably 50 to 92% and more preferably 65 to 85%.

The material for simulating a living tissue prepared in accordance with the present invention is characterized by the fact that it has the electromagnetic properties (specific inductive capacity, conductivity, thermal conductivity, specific heat and hardness) and the ultrasonic properties (density and acoustic velocity) substantially agreed with those of the simulated living tissue. It is well known that the properties listed above are important parameters. The density (Density of Soft Living Tissue: $0.98 \times 10^3$ to $1.1 \times 10^3$ (kgm$^{-3}$)) is an important parameter which affects the transmittance for X-ray and is in inverse proportion to the thermal diffusion coefficient and which affects the velocity, transmission, reflection and attenuation of the ultrasonic wave (H. S. Ho et al., "Trans. Microwave Theory. Tech.", MTT19, 224 (1971); and J. B. Leonard et al, "IEE Trans. Biomed. Eng." BME-31, 533 (1984)). The hardness or bulk modulus (Hardness of Soft Living Tissue: $2.6 \times 10^9$ Nm$^{-2}$)) also affects the reflection, transmission and attenuation of the ultrasonic wave, and it is well known that acoustic velocity is in proportion to $\frac{1}{2}$ power of the bulk modulus.

The specific inductive capacity (Specific Inductive Capacity of Soft Living Tissue: 64 to 200 at 10 MHz and 30 to 80 at 1 GHz) affects the attenuation, reflection and impedance of an electromagnetic wave. It is well known that the specific inductive capacity is in proportion to the thermal loss and that the transmission depth of an electromagnetic wave is in proportion to ½ power of the specific inductive capacity.

The conductivity (Conductivity of Soft Living Tissue: 0.5 to 0.9 (ohm$^{-1}$m$^{-1}$) at 10 MHz, 1 to 2 (ohm$^{-1}$m$^{-1}$) at 1 GHz and 10 (ohm$^{-1}$m$^{-1}$) at 10 GHz) affects the attenuation, transmission and impedance of an electromagnetic wave, and the transmission depth is in proportion to $-\frac{1}{2}$ power of the conductivity.

The thermal conductivity (Thermal Conductivity of Soft Living Tissue: 0.5 to 1.3 (Jm$^{-1}$s$^{-1}$K$^{-1}$) at 1 MHz and 0.48 to 0.66 (Jm$^{-1}$s$^{-1}$K$^{-1}$) at 1 GHz) affects the generation and diffusion of heat, and the temperature of a living tissue is in proportion to ½ power of the thermal conductivity.

The specific heat (Specific Heat of Soft Living Tissue: 3.2 to 3.7 (Jg$^{-1}$K$^{-1}$)) also affects the generation and diffusion of heat, and the temperature of a living tissue is in proportion to $-\frac{1}{2}$ power of the specific heat.

It is well known that the aforementioned properties of a soft living tissue are essentially determined by the water content of the living tissue (that is, the properties of living tissues are substantially approximate to those of water). The material for simulating a living tissue, provided by the present invention, has the aforementioned properties which are approximately agreed with those of the living tissue since it contains a large amount of water. The water content of the material provided by the present invention can be agreed with that of a specific soft living tissue (from 51 to 82 wt%, generally from 70 to 80 wt%) so that the material has the properties which are closer to those of the living tissue as compared with pure water.

In the practice of the present invention, a hydrogel having a pertinent shape may be molded by the use of a mold having a desired mold cavity. Alternatively, a hydrogel having a certain desired shape is formed and then the hydrogel may be cut by scissors or a sharp cutter to have a final desired shape.

The only material for forming a hydrogel, i.e. the gel forming ingredient, used in the present invention is the polyvinyl alcohol as defined in the claims. However, other ingredients or additives, which do not hinder gelation of the polyvinyl alcohol, may be present in the aqueous solution of polyvinyl alcohol similar to the aforementioned case where a fat is added, the amount of the coexisting additives being, for example, controlled in the range of not more than one half of the weight of the polyvinyl alcohol contained in the aqueous solution.

Examples of the additives which do not hinder gelation of the polyvinyl alcohol and may be contained in the gel forming solution are alcohols such as isopropyl alcohol, glycerin, propylene glycol and ethyl alcohol; proteins such as casein, gelatin and albumin; lipids such as lecithin, monostearin and tristearin; saccharides and polysaccharides such as glucose, agar and carrageenan; organic compounds such as butyl-p-hydroxybenzoate, phthalocyanine blue and flavanthrone; and inorganic compounds, inorganic salts and organic salts such as nickel salts, copper salts, manganese salts, iron salts, graphite, activated carbon, silica-alumina, zeolite and calcium silicate. Well-known other additives for the precise adjustment of the electromagnetic property may also be added, the examples being polyethylene powders, aluminum powders, acetylene black, sodium carbonate and sodium chloride (A. W. Guy, "IEEE Trans Microwave Theory Tech.", MTT-19, 205 (1971); J. B. Leonard et al, "IEEE Trans. Biomed. Eng.", BME-31, 533 (1984); F. K. Storm et al., "Int. J. Radiation Oncology Biol. Phys.", 8, 865 (1982); E. L. Madsen et al,. "Med. Phys.", 5, 391 (1978); M. Michele et al., "Radiology", 134, 517 (1980); and P. E. Schuwert, "Ultrasonics", 275 (1982)).

One or more of the aforementioned additives may be directly, or in the form of an aqueous solution or suspension, added in the aqueous solution of polyvinyl alcohol under agitation so as to be dispersed uniformly therein, and then the aqueous solution or suspension may be subjected to the subsequent freezing and the other processing steps.

Although the material for simulating a living tissue, according to the invention, contains a large amount of water, it has a shape retaining property at 37° C. to be molded to have a desired shape and to be used for a long time while retaining the molded shape.

The material provided by the invention is excellent in softness and reversible elasticity and can be closely fitted on the surface of the skin as far as it is molded to have a contour to profile the treated site, and also has a sufficient mechanical strength to be applied to the desired site repeatedly.

The material provided by the invention may be sterilized by a sterilizing solution, such as a solution of chlorhexidine or Osvan (Tradename), or irradiation with gamma-ray without being broken or deteriorated to be ready for fitting on the surface of the skin.

The material provided by the invention may be prepared from an aqueous solution of a polyvinyl alcohol only by thermal hysteresis at low temperature or repeated freezing-thawing or partial dehydration under a reduced pressure without the use of any acid, alkali, chemical reagent or cross-linking agent harmful to the living tissue. Accordingly, there is no need for removing any harmful ingredient from the molded product, and the molded product can be applied to a surface of the human body without causing inflammation for a long time and thus it may be applied repeatedly on the surface of the skin.

According to the present invention, the aforementioned material simulating a living tissue is applied to a surface of a human body. Then the material is pressed onto the body surface so that the material is intimately contacted with the body surface with substantially no spaces present therebetween, if necessary followed by applying the material to the body, for example, with a medical adhesive tape. Since the material has proper softness and elasticity, both the material, i.e. hydrogel and the body are deformed each other by pressing the former onto the latter so that the material is intimately contacted with the body surface. Electromagnetic wave or ultrasonic wave is then generated and irradiated to the body through the material.

The conditions such as intensity, treatment time or dosages under which electromagnetic wave or ultrasonic wave is irradiated vary depending on the specific lesion, the specific site thereof. located, etc. In the method of the present invetion, such conditions for treatment may be properly selected within the conditions commonly known for those in the art. According to the present invention, the irradiation of electromagnetic wave and ultrasonic wave is effected efficiently so that treatment time is shortened and the living tissue other than the lesion site is not adversely affected by the irradiation.

In view of the attenuation of electromagnetic wave or ultrasonic wave by the material of the present invention interposed between a source for generating the wave and the body surface, it is preferred that after the material is placed and pressed onto the body surface, a surface of the material simulating the living tissue opposite to a surface contacting the body surface be substantially flat and parallel to a plane normal to an imaginary line connecting the source of generating the wave and a lesion site in the human body.

EXAMPLES OF THE INVENTION

The present invention will now be described with reference to some examples thereof. In the following Examples, "%" stands for "% by weight" unless otherwise stated.

EXAMPLE 1

A 29% aqueous solution (containing 0.9% of NaCl) of a polyvinyl alcohol having an average polymerization degree of 2,000 and a degree of hydrolysis of 99 mol % was cast into a casting mold for molding a cylinder having a diameter of 15 cm and a height of 12 cm. The cast mass was subjected to two cycle freezing and thawing operations to obtain a hydrogel having a high water content. The water content of the hydrogel was 70 to 71% which was approximate to that of the liver (Water Content: 70 to 77%), the lens (Water Content: 67 to 70%) and the prostate (Water Content: 69 to 76%) of a human body.

The electromagnetic properties of the thus obtained hydrogel were measured and compared with those of a liver resected from a dog immediately after the dog had been killed and also compared with those of pure water. The results were that the properties of the product of this Example were well agreed with those of the comparative living tissues, as will be seen from the following data.

Conductivity ($ohm^{-1}m^{-1}$, at 10 MHz):
Example of the Invention: 0.7
Dog Liver: 0.6
Pure Water: 1.5
 Specific Inductive Capacity (at 10 MHz)
Example of the Invention: 70
Dog Liver: 64
Pure Water: 79
 Density ($kgm^{-3}$)
Example of the Invention: 1,040
Dog Liver: 1,030
Pure Water: 1,000
 Thermal conductivity ($Jm^{-1}s^{-1}K^{-1}$)
Example of the Invention: 0.8
Dog Liver: 0.7
Pure Water: 0.6
 Specific Heat at Constant Pressure ($Jg^{-1}K^{-1}$)
Example of the Invention: 3.7
Dog Liver: 3.5
Pure Water: 4.2
 Bulk Modulus (dyne $cm^{-2}$)
Example of the Invention: $2.5 \times 10^{10}$
Dog Liver: $2.6 \times 10^{10}$
Pure Water: $2.0 \times 10^{10}$

EXAMPLE 2

314 g of a 18.6% aqueous solution of a polyvinyl alcohol having an average polymerization degree of 1,000 and a degree of hydrolysis of 98 mol % was cast into a casting mold for molding a circular disk having a thickness of 1 cm and a diameter of 20 cm. The mold was then cooled to $-30°$ C. to form a frozen mass from which 22 g of water was removed under a reduced pressure of 0.1 mmHg. Then, the temperature of the mold was returned back to the room temperature, and the dehydrated mass in the mold was discharged from the mold to obtain a circular disk shape gel having a water content of 80%. The thus prepared gel was stored in a sealed container. The water content of the gel was substantially equivalent to those (ranging from 78% to 81%) of skeletal muscles, small intestine, stomach, uterus and kidney of human body.

The thus prepared circular disk was put into a polyethylene film pouch and the pouch was sealed. After sterilizing the disk by irradiating with 3 Mrad gamma-ray, the pouch was opened and a small piece (10 g) was cut from the disk. The small test piece was then transferred to a bouillon culture medium and cultured at 37° C. for seven days. No microorganism was grown. The density of the gel was measured using another cut piece ($40 \times 40 \times 10$ mm) at 37° C. to find that the density was $1.03 \times 10^3$ ($kgm^{-3}$) which was slightly higher than that of pure water and agreed with that of a soft living tissue ($1.03 \times 10^3$ ($kgm^{-3}$)). The acoustic velocity in the sample was measured by the hydro-ultrasonic wave total reflection angle detection system to find that the acoustic wave velocity was 1,600 ($ms^{-1}$) which was slightly higher than that in pure water (1,500 ($ms^{-1}$)) and well agreed with that in soft living tissues (In the Liver: 1,600($ms^{-1}$), In the skeletal Muscles: 1,600($ms^{-1}$), In the Kidney: 1,560($ms^{-1}$) and in the Skin: 1,600($ms^{-1}$)). It was thus confirmed that the hydrogel prepared by this Example was a material having an acoustic impedance (Density $\times$ Acoustic Wave Velocity) of $1,648 \times 10^3$ ($kgm^{-2}s^{-1}$) which was well agreed with the acoustic impedances (1,600 to $1,700 \times 10^3$ ($kgm^{-2}s^{-1}$)) of soft living tissues. The advantageous property of the material of this invention, as a material for simulating living tissues, should be appreciable when the acoustic impedance thereof is compared with those of a silicone rubber ($1,100 \times 10^3$ ($kgm^{-2}s^{-1}$)), polystyrene ($2,460 \times 10^3$ $kgm^{-2}s^{-1}$)) and a butadine-acrylonitrile rubber ($2,000 \times 10^3$ ($kgm^{-2}s^{-1}$)).

Then, the sample test piece was used to measure the output strength of ultrasonic wave based on the radiation power to find that an attenuation (absorption) factor was 3 $dBcm^{-1}$(at 5 MHz). The value was closer to those of soft living tissues (Liver: 3 $dBcm^{-1}$, Kidney: 4.5 $dBcm^{-1}$) than to that of pure water (0.3 $dBcm^{-1}$). The advantageous property of the material of this invention, as a material for simulating living tissues in this respect, should be appreciable when the value was compared with those of a natural rubber (155 $dBcm^{-1}$), a silicone rubber (0.8 $dBcm^{-1}$) and a butadiene-acrylonitrile rubber (70 $dBcm^{-1}$).

EXAMPLE 3

A 25% aqueous solution of a polyvinyl alcohol having an average polymerization degree of 2,600 and a degree of hydrolysis of 99 mol % was cast in a casting mold for molding a cylinder having a diameter of 30 cm and a height of 30 cm, and the cast mass was frozen at $-40°$ C., followed by thawing, to prepare a hydrogel. The hydrogel had a modulus of elasticity ($10^5 Nm^{-2}$) of 0.4 and a hardness resembling that of smooth muscle, and it did not collapse even when it had been held under a compressive pressure of 50 $kgcm^{-2}$ for 30 minutes although it had a free and rubber-like deformability. The results showed the advantage of the material prepared in accordance with this invention contrary to the hydrogels prepared from agar and carrageenan. The latter-mentioned hydrogels easily collapsed under the same conditions. The tensile strength of the hydrogel of this Example was 30 kgcm$^{-2}$.

EXAMPLE 4

Generally following the procedures as described in Example 3, ten test pieces of hydrogel (30×30 mm) having a thickness of 0.3 mm were prepared.

The test pieces were sterilized with chlorhexidine, and rinsed with a physiological saline solution under germ-free condition. One test piece was implanted under the skin of the back of a rabbit. After the lapse of 16 months, the surrounding living tissues were inspected to find no foreign body reaction such as inflammation or cellular infiltration and no excessive growth of connective tissue.

Likewise, an adult mongrel dog was intubated under general anesthesia, and the left fourth intercostal space of the dog was cut and opened for removing a portion of the pericardium by about 2 cm under controlled respiration, whereby a defect was made and the aforementioned sterilized test piece was sutured on the defect with Tevdek string. The results of anatomic inspection, after the lapse of one year, revealed that no abnormality was found in the vicinity of the hydrogel prepared by the invention and incorporated in the dog. Similarly, in a case where the same test piece was sewn to pleura of an adult dog, no foreign body reaction or adhesion was found when the operated portion was inspected after the lapse of seventeen months.

The inside surface of the knee joint of a rabbit (Body Weight: 2.5 kg) was opened along the longitudinal direction by 3 cm and the inside of the quadriceps femoris muscle was opened along the longitudinal direction. Then the patella of the rabbit was dislocated outwardly, and the lipid tissue at the front portion of the knee joint was removed while the knee joint was kept in the bent position. After cutting the cruciate ligament, the capsula articularis other than the back capsula articularis and the semilunar plate were resected. Then, the cartilage of the femur joint was deleted, and the aforementioned sterilized test piece was inserted and fixed on the face of the femur joint in place of the deleted cartilage, and then the knee joint was fixed in such condition that the joint was bent to subtend an opening angle of 150 degrees by applying a plaster bandage from the upper portion of the femur to the foot. The plaster bandage was removed after the lapse of four weeks. At that time, no rubefaction or local pyrexia was found although a slight swelling was observed at the joint, and the healing by first intention was satisfactory with no secreting fluid. The knee joint was bent to subtend about 120 degrees and the protective limping motion was observed. The movable angular range by forcible bending was 150° to 90°. A histological specimen was excised and fixed by formalin, encapsulated with paraffin, dyed with haematoxyline-eosine stain and then dyed with Mallory-azan stain. The thus treated specimen was inspected through a microscope to confirm that the molding joint face of the femur was covered by the connective tissue and that there was found no reactive osteogenesis and no inflammation in the bone-marrow. From the results of the inspection, it was confirmed that the hydrogel prepared by the present invention was excellent in adaptability to living tissues.

Hairs were removed from the scalp of an adult mongrel dog having a body weight of 17 kg and put under general anesthesia by intravenous injection of pentothal sodium. The scalp of the right top was cut by 7 cm along the longitudinal direction, and the temporal muscle was peeled off. Then, the parietal bone was pierced using a drill and a defect having the dimensions of a hen's egg was formed through the parietal bone using a bone forceps. The dura mater encephali was resected to form an opening of 1.5×2 cm. The opening was covered by the aforementioned hydrogel piece (having a high water content), with the four corner portions being sutured, and then the M. temporalis and the scalp were sewn together.

After the lapse of 8 months, the dog was killed and the hydrogel piece and the dura mater encephali and the parenchyma surrounding the hydrogel piece were excised. The results of visual observation and the results of microscopic observation of a specimen dyed with haematoxylin-eosin stain revealed that the hydrogel did not adhere to the surface of the brain. Although the surface of the hydrogel was encapsulated by fibrous tissues, no substantial adhesion thereof to the pia mater encephali was found and cellular infiltration and growth of Glia cells were not found.

The chest of an adult mongrel having a body weight of 13 kg and put under general anesthesia by intravenous injection of pentobarbital was opened, and a major portion of the pericardium at the left ventricle side was resected so that only the marginal rims for suturing were left. The thus formed defect of the pericardium was repaired by the use of the aforementioned hydrogel membrane.

Test specimens excised from the repaired portion of the sacrificed body after the lapse of 8 months were observed visually and through an optical microscope and scanning type electron microscope. The results were that the hydrogel had not adhered to the tissues of the heart and the surface of the hydrogel membrane was covered by an endothelial tissue and was smooth. No histological cellular reaction was found, and a thin endothelium tissue was found at the side facing to the heart.

The chest of an adult mongrel having a body weight of 15 kg was opened and a defect was formed at the muscular portion of the diaphragm, and the thus formed defect was repaired by the aforementioned hydrogel membrane. A test specimen excised from the repaired portion of the sacrificed body after the lapse of 8 months was inspected to reveal that the repairing hydrogel did not adhere to the tissue of the lung. The hydrogel piece was encapsulated by fibrous tissues, but no histological reaction was found.

EXAMPLE 5

A molded product was prepared by casting a 15% aqueous solution of a polyvinyl alcohol having an average polymerization degree of 1,200 and a degree of hydrolysis of 99% into a casting mold for molding an arcuated membrane having a radius of curvature of 8 mm, a uniform thickness of 0.2 mm and a diameter of 13 mm, followed by two cycle freezing and thawing processings. The thus prepared molded article was fitted on the cornea of an eye of a volunteer for 10 hours. After removing the hydrogel product, the cornea was dyed with the fluorescein stain and inspected through a slit lamp microscope to find that the cornea had no portion stained by the dye. It should be apparent from the results that the material for simulating a living tissue prepared in accordance with the present invention is excellent in adaptability to the living body, and that it is well suited for use in the condition of contacting the living tissue in view of the combined consideration of the results obtained in this Example and the result obtained in Example 4.

EXAMPLE 6

With reference to the single figure, the method of the present invention is explained.

In accordance with the process of Example 3, a disklike hydrogel 10 with the water content of 75% (diameter of 12 cm; thickness of 4 cm) was obtained. The disk 10 was placed on the mamma 11 of a patient lying in a horizontal supine position and lightly pressed and secured in position with the center of the disk 10 substantially in register with the areola. At this time, due to relative deformation of the hydrogel 10 and the mammary surface 12, the mammilla, areola and the mamma in its vicinity were transiently apparently embedded and fused into the hydrogel plate, and the flatness of the upper surface 13 of the hydrogel 10 was maintained.

A vibrator 14 was then applied to the upper surface 13 of the hydrogel 10 and ultrasonic vibration was initiated at a frequency of 5 MHz. While energizing a motor 15, a scanner 16 with the vibrator 14 was made to run along a bar 17 with the tip 18 of the vibrator 14 in contact with the flat surface 13 of the hydrogel 10 to obtain an ultrasonic tomogram. The tumor echo due to a tumor 19 and further the lung echo were clearly observed on the Braun tube (not shown) next to the transmission wave and the skin echo.

The vibration was continued for 5 minutes to generate heat in the cells of the lesion site under the effect of the ultrasonic wave. After the electrical power source was turned off, a thermister needle was inserted into the lesion site and the temperature was measured. When the temperature of the lesion site was not higher than 41° C. the thermister needle was extracted and the heating was again performed for five minutes.

By repetition of the alternate operations of intermittently heating the lesion site and measuring its temperature, the lesion site was maintained at a temperature of 41.5° to 43° C. for two hours.

After this hyperthermia was carried out thrice every three days. The lesion was reduced in size, thus demonstrating the effectiveness of the ultrasonic diagnosis and therapy making use of the hydrogel of the present invention. This therapy was further continued every three days with the cojoint irradiation of cobalt 60, Endoxan dripping and one shot injection of Adriamycin. Thus, it was observed after one month that the lesion was markedly reduced in size.

After the termination of the ultrasonic diagnosis and therapy, the hydrogel disk was immersed for one hour in a disinfectant solution and then immersed and stored in tap water to make ready for subsequent usages.

This hydrogel was repeatedly used 13 times on the same portion of the same patient. No inflammation of the skin or rubefaction was observed.

COMPARATIVE EXAMPLE 1

A disk of the Examples 6 (12 cm in diameter and 4 cm in thickness) was produced by using butyl rubber, a well-known material for ultrasonic applications. This disk was placed on the patient's mamma and pressed similarly to Example 6. Although the mammary surface was seen to be deformed in this manner, deformation of the contact surface of the butyl rubber could not follow up with that of the mammary surface such that voids or gaps were produced here and there on the contact surface of the butyl rubber with the mammary surface.

Although the transmission wave could be observed on the Braun tube, reflection by the residual air in these voids or gaps was so severe that it was recognized difficult to discriminate the signals emitted from the tumor, while the skin echo was blurred frequently.

Some patients also suffered from gum rash or miliaria rubra due to butyl rubber.

As described above, on account of the severe reflection losses of the ultrasonic waves, therapy by ultrasonic waves had to be abandoned such that resort had to be made to diagnosis by X-ray CT scan and to chemical and radiography therapy as conventionally so that it was impossible to achieve the effect of cojoint use of various diagnosis and therapeutic artifices.

COMPARATIVE EXAMPLE 2

A disk of the Example 6 was produced using a gelatin or jelly, a well-known material for ultrasonic applications. The disk was placed on the mamma and pressed. It was seen that, although the gelatin plate and the mammary surface were intimately bonded and fused to each other and the areola was also embedded and fused into the jelly, the jelly plate in its entirety was gradually deformed, while the flatness of the upper surface thereof was lost. The jelly plate was fragile enough to collapse and be broken during the maintenance operation aimed to recover the flatness.

Although the present invention has been described with reference to the specific examples, it should be understood that various modifications and variations can be easily made by those skilled in the art without departing from the spirit of the invention. Accordingly, the foregoing disclosure should be interpreted as illustrative only and not to be interpreted in a limiting sense. The present invention is limited only by the scope of the following claims.

What is claimed is:

1. A method for applying electromagnetic wave therapy comprising applying to a surface of a human body a material simulating a living tissue made of a frozen and thawed polyvinyl alcohol hydrogel of high water content having soft reversible elasticity and shape-retaining properties, pressing said material onto the surface of the human body so that said material is intimately contacted with said surface of the human body with substantially no spaces present therebetween, generating as electromagnetic wave and irradiating said wave to the human body through said material.

2. The method according to claim 1, wherein after said material is pressed onto the surface of the human body, a surface of said material opposite to a surface contacting the human body is substantially flat and parallel to a plane normal to an imaginary line connecting a source for generating said wave and a lesion site in the human body.

3. The method according to claim 1, wherein said hydrogel contains 50 to 92 wt% of water.

4. A method for applying ultrasonic wave therapy comprising applying to a surface of a human body a material simulating a living tissue made of a frozen and thawed polyvinyl alcohol hydrogel of high water content having soft reversible elasticity and shape-retaining properties, pressing said material onto the surface of the human body so that said material is intimately contacted with said surface of the human body with substantially no spaces present therebetween, generating an ultrasonic wave and irradiating said wave to the human body through said material.

5. The method according to claim 4, wherein after said material is pressed onto the surface of the human body, a surface of said material opposite to a surface contacting the human body is substantially flat and parallel to a plane normal to an imaginary line connecting a source for generating said wave and a lesion site in the human body.

6. The method according to claim 4, wherein said hydrogel contains 80 to 92 wt% of water.

7. A method for applying electromagnetic wave therapy comprising applying to a surface of a human body a material simulating a living tissue made of a frozen and partially dehydrated polyvinyl alcohol hydrogel having soft reversible elasticity and shape-retaining properties, pressing said material onto the surface of the human body so that said material is intimately contacted with said surface of the human body with substantially no spaces present therebetween, generating an electromagnetic wave and irradiating said wave to the human body through said material.

8. The method according to claim 7, wherein after said material is pressed onto the surface of the human body, a surface of said material opposite to a surface contacting the human body is substantially flat and parallel to a plane normal to an imaginary line connecting a source for generating said wave and a lesion site in the human body.

9. The method according to claim 7, wherein said hydrogel contains 50 to 92% of water.

10. A method for applying ultrasonic wave therapy comprising applying to a surface of a human body a material simulating a living tissue made of a frozen and partially dehydrated polyvinyl alcohol hydrogel having soft reversible elasticity and shape-retaining properties, pressing said material onto the surface of the human body so that said material is intimately contacted with said surface of the human body with substantially no spaces present therebetween, generating an ultrasonic wave and irradiating said wave to the human body through said material.

11. The method according to claim 10, wherein after said material is pressed onto the surface of the human body, a surface of said material opposite to a surface contacting the human body is substantially flat and parallel to a plane normal to an imaginary line connecting a source for generating said wave and a lesion site in the human body.

12. The method according to claim 4, wherein said hydrogel contains 50 to 92 wt% of water.

* * * * *